United States Patent [19]
Ebata et al.

[11] Patent Number: 5,468,881
[45] Date of Patent: Nov. 21, 1995

[54] METHOD OF PRODUCING CIS-WHISKEY LACTONE

[75] Inventors: Takashi Ebata; Katsuya Matsumoto; Koshi Koseki; Hiroshi Kawakami; Hajime Matsushita, all of Yokohama; Hajime Yoshikoshi; Masakazu Okaniwa, both of Tokyo, all of Japan

[73] Assignees: Japan Tobacco Inc.; Yuji Gosei Kogyo Co., Ltd., both of Tokyo, Japan

[21] Appl. No.: 920,578

[22] PCT Filed: Dec. 27, 1991

[86] PCT No.: PCT/JP91/01780

§ 371 Date: Aug. 27, 1992

§ 102(e) Date: Aug. 27, 1992

[87] PCT Pub. No.: WO92/12143

PCT Pub. Date: Jul. 23, 1992

[30] Foreign Application Priority Data

Dec. 27, 1990  [JP]  Japan .................................. 2-407648

[51] Int. Cl.⁶ ................................................ C07D 307/02
[52] U.S. Cl. ............................................ 549/295; 549/326
[58] Field of Search ................................. 549/295, 326

[56] References Cited

U.S. PATENT DOCUMENTS

| | | | |
|---|---|---|---|
| 3,926,947 | 12/1975 | Lipska | 536/1.11 |
| 4,994,585 | 2/1991 | Koseki et al. | 549/323 |
| 5,112,994 | 5/1992 | Koseki et al. | 549/323 |

FOREIGN PATENT DOCUMENTS

| | | |
|---|---|---|
| 63-41473 | 2/1988 | Japan . |
| 63-222162 | 9/1988 | Japan . |
| 3167180 | 7/1991 | Japan . |
| 4154776 | 5/1992 | Japan . |

OTHER PUBLICATIONS

Mitsunobu (1981) Synthesis, vol. No. 1, pp. 1–28.
Gunther, et al. (1986) Liebigs Ann. Chem, pp. 2112–2122.
Salaun, et al. (1989) Tetrahedron vol. 45, No. 10, pp. 3151–3162.
Derwent Publications Ltd., Abstract of JP 63–068578 Mar. 1988.
Helvetica Chimica Acta—vol. 72 (1989) pp. 1362–1370.
Tetrahedron, vol. 30, pp. 3547–3552, Pergamon Press 1974.
Carbohydrate Research, 167 (1987) pp. 187–196.
Tetrahedron vol. 46, No. 1, pp. 231–243, 1990.
"Formal Total Synthesis of 1β–Methylcarbapanem Via a Novel Route to Deoxylamino Sugars" J. Org. Chem. 1989, 54, pp. 2103–2212.
"Nature", No. 4192 Mar. 4, 1950, p. 369.
Liebigs Ann. Chem. 1986, pp. 2112–2122.
"Synthesis" (1986), pp. 1052–1054.
"Tetrahedron Letters", vol. 28, No. 20, pp. 2299–2300, 1987.
"Chemical Abstract" vol. 89, 1978, pp. 690, 43996j.
"Synthesis of the Dideoxynucleosides DDC and CNT from Clutamic Acid, Ribonolactone, and Pyrimidine Bases" J. Org. Chem. 1988, 53, pp. 4780–4786.
"Heterocycles", vol. 31, No. 9, 1990, pp. 1585–1588.
"Advanced Organic Chemistry" p. 400 1977.
"Tetrahedron" vol. 43, No. 19, pp. 4497–4506, 1987.
"Carbohydrate Research" 129 (1984) pp. 73–86.
"Synthetic Studies on Cembranolides Stereoselective Synthesis of Epoxy Ester Intermediates" J. Org. Chem. 1984, 49, pp. 747–753.
Angew. Chem. Int. Ed. Engl. 28 (1989) No. 1, pp. 69–71.
Chemistry Letters, pp. 307–310, 1990.
"Tetrahedron" vol. 38, No. 15, pp. 2395–2402, 1982.

Primary Examiner—C. Warren Ivy
Assistant Examiner—A. A. Owens
Attorney, Agent, or Firm—Birch, Stewart, Kolasch & Birch

[57] ABSTRACT

After the lactone portion of trans-whiskey lactone is hydrolyzed with potassium hydroxide, this portion is reacted with isopropyl bromide and mixed with an alkyl group, thereby obtaining isopropyl (3S,4S)-4-hydroxy-3-methyloctanoate. Then, the isopropyl (3S,4S)-4-hydroxy-3-methyloctanoate is reacted with diethyl azodicarboxylate in the presence of triphenylphosphine and azodicarboxylate, thereby obtaining isopropyl (3S,4S)-4-(3',5'-dinitrobenzoyloxy)-3-methyloctanoate. The isopropyl (3S,4S)-4-(3',5'-dinitrobenzoyloxy)-3-methyloctanoate is hydrolyzed in 2% potassium hydroxide, and as a result, cis-whiskey lactone (A) represented by the following general formula is obtained. According to this method, cis-whiskey lactone, one of the perfume components of whiskey and wine, can be produced selectively and easily.

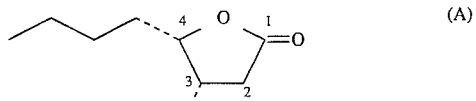

(A)

10 Claims, No Drawings

METHOD OF PRODUCING CIS-WHISKEY LACTONE

TECHNICAL FIELD

The present invention relates to a method of producing natural type cis-whiskey lactone contained in whiskey, wine, etc.

PRIOR ART

Whiskey lactone (3-methyl-4-octanolide) is one of the perfume components of whiskey and wine.

There are stereomers of the natural whiskey lactone, which are of the trans-type or cis-type in accordance with the configuration of the methyl group at the 3-position thereof and butyl group at 4-position thereof. As compared to trans-whiskey lactone [(3S,4R)-3-methyl-4-octanolide] (D), generally, a lower amount of cis-whiskey lactone [(3S,4S)-3-methyl-4-octanolide] (A) is contained, for example, in whiskey and wine. However, cis-whiskey lactone (A) is superior in perfume characteristics.

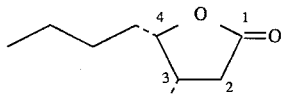
(A)

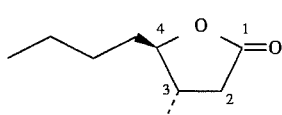
(D)

However, a means for selectively synthesizing natural type cis-whiskey lactone (A) having superior properties to those of the trans-type isomer (D) as described above has not been known.

DISCLOSURE OF THE INVENTION

It is the object of an present invention to provide a method of producing cis-whiskey lactone which is able to selectively and easily synthesize natural type cis-whiskey lactone.

In order to solve the above problem, the inventor carefully reviewed and paid attention to the fact that trans-whiskey lactone and cis-whiskey lactone differ only in the absolute configuration of the butyl group at the 4-position thereof, and determined that the trans-whiskey lactone can be converted to the cis-whiskey lactone by reversing the solid configuration of the butyl group at the 4-position, thereby completing the present invention.

The present invention comprises: A method of producing cis-whiskey lactone, comprising, (a) hydrolyzing the lactone portion of 3,4-trans-whiskey lactone [(3S,4R)-3-methyl-4-octanolide] represented by general formula (D) and adding an alkyl group to the hydrolyzed portion, thereby obtaining the 3,4-trans compound represented by general formula (C), (b) reacting said 3,4-trans compound (C) obtained in step (a) with an acyl compound in the presence of triphenylphosphine and azodicarboxylate, thereby obtaining 3,4-cis compound (B) presented by general formula (B), and (c) hydrolyzing 3,4-cis compound (B) obtained in step (b) and lactonizing the hydrolyzed compound, thereby obtaining 3,4-cis-whiskey lactone [(3S, 4S)-3-methyl-4-octanolide] (A) represented by general formula (A):

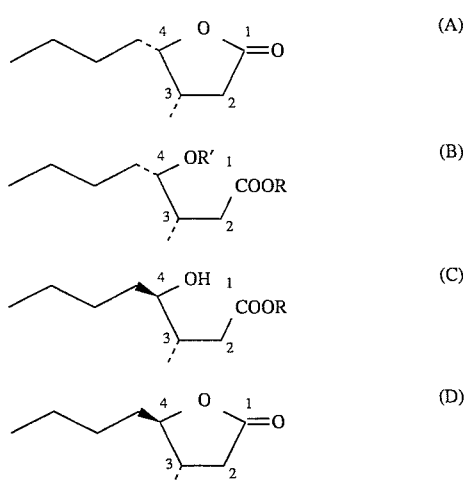

wherein R represents a general alkyl group and R' represents a general acyl group.

The method of producing cis-whiskey lactone of the present invention will be described below in detail.

Trans-whiskey lactone (D) used as a starting substance in the present invention can be produced, for example, by a well-known producing method described in "Heterocycles No. 31, pp. 1585–1588 (1990)".

Hydrolysis of the lactone portion in step (a) can be achieved, for example, by using a solution of an alkali such as sodium hydroxide, or potassium hydroxide. As a result, the lactone ring of the trans-whiskey lactone is broken between the carbon at the 1-position of the lactone and oxygen, and trans compound ($D_2$) as indicated in the following formula can be obtained.

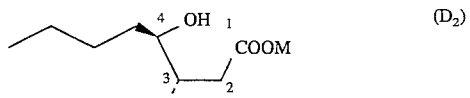
($D_2$)

In this formula, M represents an alkali metal.

Then, trans compound ($D_2$) is made to react with, for example, an alkyl halide such as isopropyl bromide or butyl bromide in an appropriate solvent, thereby adding an alkyl group to the carbonyl group at the 1-position of compound ($D_2$) and obtaining trans compound (C). The appropriate solvent to be used in this step is, for example, an organic solvent such as dimethyl formamide or dimethyl sulfoxide, but it is not particularly limited.

In the reverse reaction, i.e., Mitunobu reaction of the butyl group at the 4-position of trans compound (C) in the step (b), trans compound (C) obtained in step (a) is made to react with, for example, acetic acid, benzoic acid, or an acyl derivative thereof in the presence of triphenylphosphine and azodicarboxylate, in an appropriate solvent, thereby reversing the configuration of the butyl group at the 4-position of trans compound (C). As a result, cis compound (B) in which the butyl group at the 4-position thereof and the methyl group at the 3-position thereof mutually configured in the cis-type can be obtained. The appropriate solvent to be used in this step is, for example, an organic solvent such as ether, tetrahydrofuran, or toluene, but it is not particularly limited.

In step (c), at first, the alkyl group added to the 1-position carboxyl group of the cis compound (B) and the acyl group at the 5-position can be eliminated, for example, by hydrolyzing the cis compound (B) under basic conditions.

A basic compound to be used for the elimination reaction in the step (c) is, for example, a metallic oxide (potassium hydroxide, sodium hydroxide, lithium hydroxide, etc.), a carbonate (potassium carbonate, sodium carbonate, etc.), or a metal alkoxide (alkoxide sodium isopropoxide, potassium butoxide, etc.)

A solvent to be used in step (c) is, for example, water, alcohol (methanol, ethanol, etc.), tetrahydrofuran, or these solvents together mixed, but it is not particularly limited.

After the above elimination reaction, the lactone ring is closed by making the reaction solution acidic, thereby obtaining cis-whiskey lactone (A). An acid substance to be used for this lactonization is, for example, a mineral acid (hydrochloric acid, sulfuric acid, etc.), an organic acid (paratoluenesulfonic acid, etc.)

In the above description, the case of converting (3S,4R)-3-methyl-4-octanolide(D) in the trans-type of whiskey lactone to (3S,4S)-3-methyl-4-octanolide (A) in the cis-type was described. However, conversion of (3R,4S)-3-methyl-4-octanolide shown by the following general formula (D') to (3R,4R)-3-methyl-4-octanolide shown by general formula (A') can also be performed in a similar manner to the above reaction.

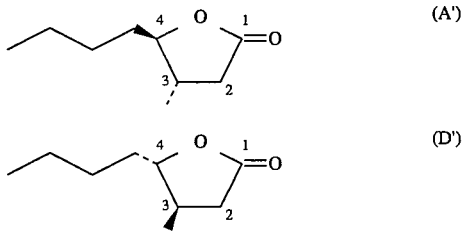

As described above, according to the method of producing cis-whiskey lactone of the present invention, effects, which demonstrate that the natural type cis-whiskey lactone can be selectively and easily synthesized, can be accomplished.

DETAILED DESCRIPTION OF THE INVENTION

The present invention will be described in further detail in the following example.

Example 1

Step A: Production of isopropyl (3S,4S)-4-hydroxy-3-methyloctanoate.

1.07 g (6.86 mmol) of (3S,4R)-3-methyl-4-octanolide (trans-whiskey lactone) produced according to the method described in the above Heterocycles No. 31 were dissolved in a mixed solvent of methanol (7 ml) and water (1.4 ml). 491 mg (7.54 mmol) of potassium hydroxide were added to the obtained solution under ice cooling. This solution was stirred for 5 hours at room temperature and then concentrated. Ether was added to the obtained residue, and the obtained solution was concentrated again. After this operation was repeated once again, reduced-pressure drying was performed for 6 hours.

After this, the dried residue was dissolved in 10 ml of anhydrous dimethylformamide, 1.69 g (13.7 mmol) of isopropyl bromide were added to the solution, and this solution was stirred for one night at room temperature. Then, 30 ml of water were added to the reaction solution which was then extracted 5 times with ether. The solution which was obtained by combining each extracted solution was washed by with water and saturated saline water sequentially, dried with anhydrous sodium sulfate, and concentrated. In this way, 1.60 g of crude isopropyl (3S,4S)-4-hydroxy-3-methyloctanoate was obtained. Physical data of the obtained crude product were:

IR (film): γmax 3500(br), 2962(s), 2934(s), 2876(s), 1729(s), 1715(s), 1460(m), 1377(s), 1270(s), 1178(s), 1108(s), 975(s), 899(m)

This crude product was used in the following step without being purified.

Step B: Production of isopropyl (3S,4S)-4-(3',5'-dinitrobenzoyloxy)-3-methyloctanoate.

1.60 g of the crude product obtained in step A were dissolved in 12 ml of anhydrous tetrahydrofuran. While the solution was stirred and cooled with ice, 2.70 g (10.3 mmol) of triphenylphosphine, 2.18 g (10.3 mmol) of 3,5-dinitro benzoic acid, and 1.79 g (10.3 mmol) of diethyl azodicarboxylate were added to this solution. After stirring for three days at room temperature, this solution was poured into ice water and extracted with ether. After washing with water and saturated saline water sequentially, this extracted solution was dried with anhydrous magnesium sulfate. After concentration, the obtained residue was purified by silica-gel column chromatography (n-hexane: ether=10:1–5:1), thereby obtaining 2.15 g (76.5%) of isopropyl (3S,4S)-4-(3',5'-dinitrobenzoyloxy)-3-methyl octanoate. Physical data of the obtained product were:

$^1$H-NMR(CDCl$_3$):δ0.90(3H, t, J=6.9 Hz), 1.09(3H, d, J=6.8 Hz), 1.21(3H, d, J=6.2 Hz), 1.23(3H, d, J=6.2 Hz), 1.26–1.40(4H, m), 1.62–1.85(2H, m), 2.13–2.25(1H, m), 2.35–2.50(2H, m), 5.01(1H, m), 5.23–5.30(1H, m), 9.11–9.18(2H, m), 9.21–9.25(1H, m).

Step C: Production of (3S,4S)-3-methyl-4-octanolide (cis-whiskey lactone)

380 mg (0.93 mmol) of isopropyl (3S,4S)-4-(3',5'-dinitrobenzoyloxy)-3-methyl octanoate obtained in step B were dissolved in 5 ml of methanol. 2% sodium hydroxide was added to adjust this solution at pH14. After this solution was stirred at one night at room temperature, 1N hydrochloric acid was added to the reactant solution, and the solution was adjusted at pH1. Thereafter, the solution was stirred for one hour at room temperature. Then, after the resultant solution was extracted by ether, the extracted solution was dried by anhydrous magnesium sulfite, and concentrated. After purification by column chromatography (n-hexane: ether= 10:1–2:1), the obtained residue was distilled under reduced pressure and 122 mg (84.1%) of (3S,4S)-3-methyl-4-octanolide (cis-whiskey lactone) were obtained. Physical data of the obtained cis-whiskey lactone were:

Boiling Point: 124°–126° C./17 mmHg
$^1$H-NMR(CDCl$_3$):δ0.92(3H, t, J=7.0 Hz), 1.02(3H, d, J=6.9 Hz), 1.20–1.75(6H, m), 2.20(1H, dd, J=3.8 and 16.8 Hz), 2.51–2.64(1H, m), 2.70(1H, dd, J=7.8 and 16.8 Hz), 4.40–4.48(1H, m).

We claim:

1. A method of producing cis-whiskey lactone, comprising:

(a) hydrolyzing the lactone portion of 3,4-trans-whiskey lactone represented by formula (IV) and adding an alkyl group to the hydrolyzed portion, thereby obtaining the 3,4-trans compound represented by formula (III),

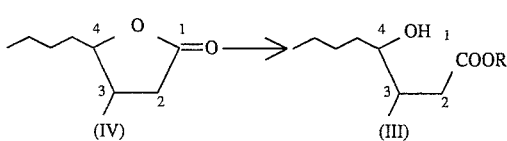

(IV) → (III)

wherein R represents an alkyl group;

(b) reacting said 3,4-trans compound (III) obtained in step (a) with an acyl compound in the presence of triphenylphosphine and azodicarboxylate, thereby obtaining the 3,4-cis compound represented by formula (II),

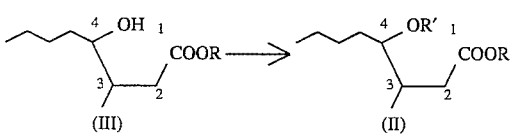

(III) → (II)

wherein R represents an alkyl group and R' represents an acyl group; and (c) hydrolyzing and lactonizing said 3,4-cis compound (II) obtained in step (b), thereby obtaining 3,4-cis-whiskey lactone represented by formula (I),

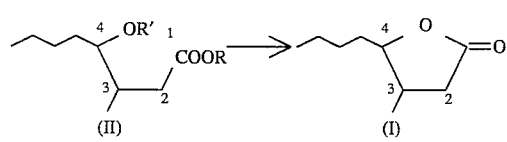

(II) → (I)

wherein R and R' are the same as in step (b).

2. A method of producing cis-whiskey lactone, comprising:

(a) hydrolyzing the lactone portion of (3S,4R)-3-methyl-4-octanolide represented by formula (D) and adding an alkyl group to the hydrolyzed portion, thereby obtaining the 3,4-trans compound represented by formula (C),

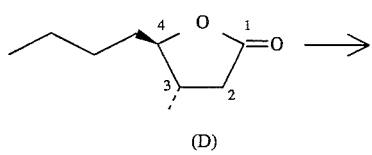

(D) →

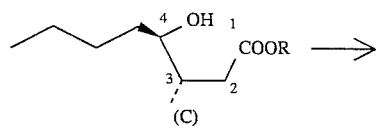

(C)

wherein R represents an alkyl group;

(b) reacting said 3,4-trans compound (C) obtained in step (a) with an acyl compound in the presence of triphenylphosphine and azodicarboxylate, thereby obtaining the 3,4-cis compound represented by formula (B),

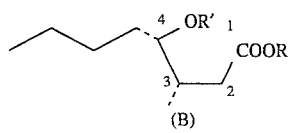

(B)

wherein R represents an alkyl group and R' represents an acyl group; and (c) hydrolyzing and lactonizing said 3,4-cis compound (B) obtained in step (b), thereby obtaining (3S, 4S)-3-methyl-4-octanolide represented by formula (A),

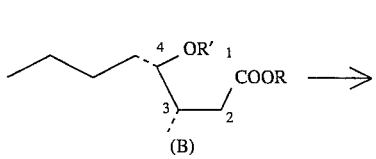

(B) →

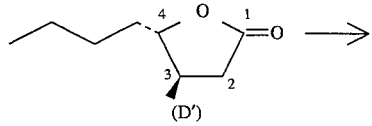

(A)

wherein R and R' are the same as in step (b).

3. A method of producing cis-whiskey lactone, comprising:

(a) hydrolyzing the lactone portion of (3R,4S)-3-methyl-4-octanolide represented by formula (D') and adding an alkyl group to the hydrolyzed portion, thereby obtaining the 3,4-trans compound represented by formula (C'),

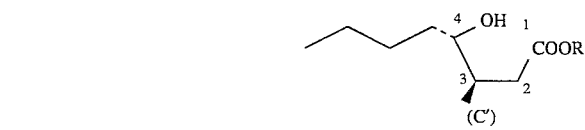

(D') →

(C')

wherein R represents an alkyl group;

(b) reacting said 3,4-trans compound (C') obtained in step (a) with an acyl compound in the presence of triphenylphosphine and azodicarboxylate, thereby obtaining the 3,4-cis compound represented by formula (B'),

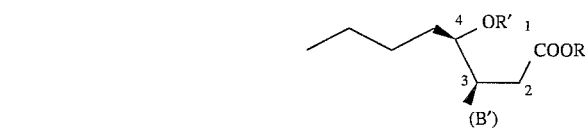

(C') →

(B')

wherein R represents an alkyl group and R' represents an acyl group; and (c) hydrolyzing and lactonizing said 3,4-cis compound (B') obtained in step (b), thereby obtaining (3R,4R)-3-methyl-4-octanolide represented by formula (A'),

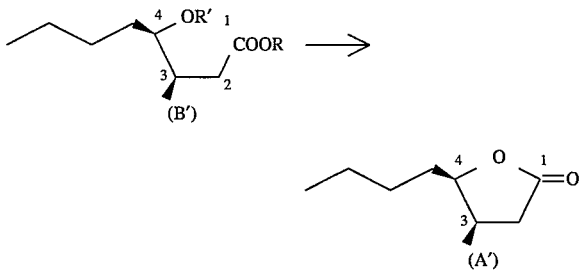

wherein R and R' are the same as in step (b).

4. The method of any one of claims 1–3, wherein said alkyl group is derived from an alkyl halide.

5. The method of claim 4, wherein said alkyl halide is a member selected from the group consisting of isopropyl bromide and butyl bromide.

6. The method of any one of claims 1–3, wherein said adding said alkyl group of step (a) is carried out in an organic solvent selected from the group consisting of dimethyl formamide and dimethylsulfoxide.

7. The method of any one of claims 1–3, wherein step (b) is carried out in an organic solvent selected from the group consisting of ether, tetrahydrofuran, and toluene.

8. The method of any one of claims 1–3, wherein said hydrolyzing of step (c) is carried out by employing a metallic oxide selected from the group consisting of potassium hydroxide, sodium hydroxide, and lithium hydroxide, a carbonate selected from the group consisting of potassium carbonate and sodium carbonate, or a metal alkoxide selected from the group consisting of sodium isopropoxide and potassium butoxide.

9. The method of claim 8, wherein said hydrolyzing is carried out in a solvent selected from the group consisting of water, an alcohol, tetrahydrofuran, and a mixture of any of the foregoing.

10. The method of any one of claims 1–3, wherein said lactonizing of step (c) is carried out by making the reaction solution acidic with an acid selected from the group consisting of a mineral acid and an organic acid.

* * * * *

UNITED STATES PATENT AND TRADEMARK OFFICE
CERTIFICATE OF CORRECTION

PATENT NO. : 5,468,881
DATED : Nov. 21, 1995
INVENTOR(S) : Ebata et al

It is certified that error appears in the above-indentified patent and that said Letters Patent is hereby corrected as shown below:

ON THE TITLE PAGE:

Item "[73] Assignees:" change "Yuji" to --Yuki--.

Signed and Sealed this

Twenty-third Day of April, 1996

Attest:

BRUCE LEHMAN

Attesting Officer    Commissioner of Patents and Trademarks